United States Patent
Borrero et al.

(10) Patent No.: US 8,834,437 B2
(45) Date of Patent: Sep. 16, 2014

(54) DISPOSABLE ABSORBENT ARTICLE WITH EXTENSIBLE AND RETRACTABLE CORE

(71) Applicant: Presto Absorbent Products, Inc., Eau Claire, WI (US)

(72) Inventors: Ricardo Borrero, Altoona, WI (US); Michael Wayne Harris, Eau Claire, WI (US)

(73) Assignee: National Presto Industries, Inc., Eau Claire, WI (US)

( * ) Notice: Subject to any disclaimer, the term of this patent is extended or adjusted under 35 U.S.C. 154(b) by 0 days.

(21) Appl. No.: 14/037,093

(22) Filed: Sep. 25, 2013

(65) Prior Publication Data

US 2014/0088538 A1   Mar. 27, 2014

Related U.S. Application Data

(60) Provisional application No. 61/705,802, filed on Sep. 26, 2012.

(51) Int. Cl.
*A61F 13/15* (2006.01)

(52) U.S. Cl.
USPC ............ 604/385.16; 604/385.22; 604/385.24; 604/385.25; 604/385.26; 604/385.27; 604/385.28; 604/385.29

(58) Field of Classification Search
USPC ............ 604/385.16, 385.22, 385.24, 385.25, 604/385.26, 385.27, 385.28, 385.29, 385.3
See application file for complete search history.

(56) References Cited

U.S. PATENT DOCUMENTS

| 5,685,874 | A | 11/1997 | Buell et al. |
| 6,932,800 | B2 | 8/2005 | Lavon et al. |
| 7,749,211 | B2 * | 7/2010 | Van Gompel et al. ... 604/385.27 |
| 7,785,309 | B2 * | 8/2010 | Van Gompel et al. . 604/385.101 |
| 7,919,669 | B2 | 4/2011 | Roe et al. |

FOREIGN PATENT DOCUMENTS

EP    0813401 B1    6/2000

OTHER PUBLICATIONS

"International Application Serial No. PCT/US2013/061748, International Search Report mailed Feb. 4, 2014", 4 pgs.
"International Application Serial No. PCT/US2013/061748, Invitation to Pay Additional Fees and Partial Search Report mailed Dec. 5, 2013", 2 pgs.
"International Application Serial No. PCT/US2013/061748, Written Opinion mailed Feb. 4, 2014", 14 pgs.

* cited by examiner

*Primary Examiner* — Jacqueline F. Stephens
(74) *Attorney, Agent, or Firm* — Schwegman Lundberg & Woessner, P.A.

(57) ABSTRACT

A disposable absorbent garment can include a waistband assembly that is configured to be worn about a waist of a subject, and an absorbent panel assembly having first and second ends that are coupled to the waistband assembly. The absorbent panel assembly can include a liquid-pervious body-side layer, a liquid impervious external layer, and an absorbent core positioned between the body-side and external layers. At least one of the absorbent panel assembly or the waistband assembly includes a contraction region, such as near the absorbent core, that is configured to be extensible and retractable along a longitudinal axis of the absorbent core. The longitudinal axis can be substantially parallel to a vertical or height axis of a wearer when the absorbent garment is worn by an upright or standing individual.

24 Claims, 6 Drawing Sheets

DISPOSABLE ABSORBENT ARTICLE WITH EXTENSIBLE AND RETRACTABLE CORE

RELATED APPLICATIONS

This application claims the benefit of priority to U.S. Provisional Patent Application Ser. No. 61/705,802, filed Sep. 26, 2012, which is hereby incorporated by reference herein in its entirety.

BACKGROUND

Incontinent individuals or infants can use an absorbent garment, such as a diaper, that is capable of absorbing or containing human waste products. Diapers can have various shapes and sizes, and are generally configured to be worn between an individual's legs and fastened about the waist. Some diapers are reusable, such as including a washable woven cloth material that can be worn in combination with a fluid-impervious outer garment. Some diapers are disposable and are intended to be discarded after a single use. Such diapers can be configured with a fluid-impermeable or fluid-impervious outer layer (bottom sheet) and an absorbent inner portion (core).

Some diapers have an hourglass shape when they are extended and flattened. The hourglass shape can minimize an amount of material that comprises the area of the diaper worn between the wearer's legs, yet provide sufficient material in the front and rear portions of the diaper to cover the front and rear sides of the wearer. Some diapers provide additional material around the legs for further leakage control. In some examples, the front and rear portions of the diaper overlap to completely encircle a wearer's waist. Fastening devices can be included on the overlap areas of the front and rear portions of the diaper. In some examples, the front or rear portions of the diaper include one or more fastening devices, and each fastening device can be secured to an opposite portion of the diaper when worn. Some fastener devices include adhesive tape tabs and hook-and-loop materials.

In some examples, fastening devices on the rear portion of the diaper can be attached to the waist portion of the diaper by way of flaps or ears. The ears can extend from the main diaper body at the rear waist, with the fastening devices joined to the edges of the ears or affixed on the body of the ears. When the rear waist portion of the diaper is joined to the front waist portion of the diaper, the ears can form a portion of a leg opening. Fastening devices and other characteristics of a wearable absorbent article can contribute to a wearer's perception of how well the article fits the wearer, and of how well the article functions.

OVERVIEW

The present inventors have recognized, among other things, that a problem to be solved can include providing a wearable absorbent article that maintains close physical contact with a wearer's body, such as even when the wearer is engaged in physical activity. The present inventors have further recognized that a problem to be solved can include providing a wearable absorbent article that instills confidence in a wearer that the article is properly positioned to receive and absorb waste products. The present subject matter can help provide a solution to these problems, such as by providing an absorbent garment with an extensible and retractable absorbent panel assembly. The extensible and retractable absorbent panel assembly can include an absorbent core that can be drawn up into the wearer's crotch area, such as using elastic portions that, when worn, are extensible and retractable in a direction substantially parallel to the wearer's longitudinal (height) axis.

In some examples, a disposable absorbent garment can be similarly sized and shaped to a traditional cloth undergarment. A garment can include at least a waist opening and two leg openings. The garment can include panels that are stretchable, or extensible and retractable, in at least one direction, and optionally in at least two different directions (e.g., substantially orthogonal directions). The garment can conform to various body shapes and sizes. The garment can include an absorbent portion that is configured to be disposed in a wearer's crotch region and to absorb human bodily excretions. At least one of the front and back panels can include an extensible and retractable portion that is configured to pull or draw the absorbent portion into or toward the wearer's crotch region.

This overview is intended to provide non-limiting examples of the present subject matter, and this overview is not intended to provide an exclusive or exhaustive explanation. The detailed description below is included to provide further information about the present disposable absorbent articles and related methods.

BRIEF DESCRIPTION OF THE DRAWINGS

In the drawings, which are not necessarily drawn to scale, like numerals may describe similar components in different views. The drawings illustrate generally, by way of example, but not by way of limitation, various embodiments discussed in the present document.

DETAILED DESCRIPTION

A disposable absorbent garment can include a waistband assembly that is configured to be worn about a waist of a subject, and an absorbent panel assembly having first and second ends that are coupled to the waistband assembly. The absorbent panel assembly can include an absorbent core configured to absorb bodily fluids. At least one of the absorbent panel assembly or the waistband assembly can include a contraction region, such as adjacent to the absorbent core, that is configured to be extensible and retractable along a longitudinal axis of the absorbent core. The contraction region can comprise an extensible and retractable base material, or can include a non-extensible base material to which one or more extensible and retractable materials, such as elastic strands, are affixed. The longitudinal axis can be substantially parallel to a vertical or height axis of a wearer when the absorbent garment is worn by an upright or standing individual. In some examples, the contraction region is configured to elastically retract the absorbent core toward the waistband assembly, or toward an upper edge of the waistband assembly.

Figure 1A:
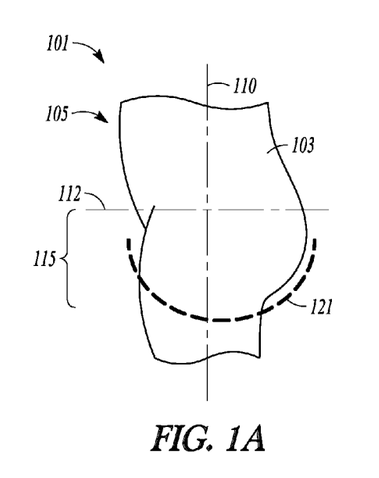
FIGS. 1A and 1B illustrate generally examples of a human torso on which an absorbent garment can be worn.
Figure 1B:
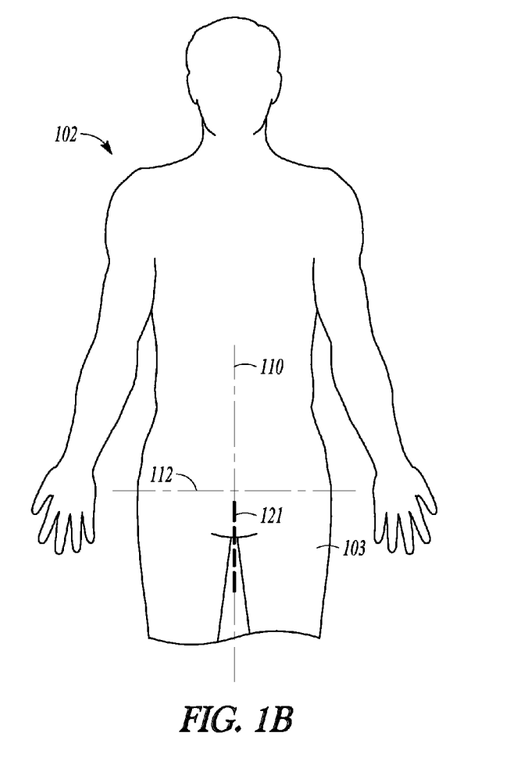

FIGS. 1A and 1B illustrate generally a side view example 101 and a front view example 102, respectively, of a body torso region 105 of a subject. The subject, referred to generally herein as a "wearer", can wear an absorbent garment or diaper. Referring first to FIG. 1A, the example 101 includes a body 103 in a substantially upright or standing position. The body 103 has a vertical or height axis 110 that extends longitudinally along the body 103, such as from the body legs toward the body head (not shown in FIG. 1A), or perpendicular to a surface on which the wearer may stand. The body 103 has a transverse axis 112 that extends substantially perpendicularly to the height axis 110. The example 101 includes the wearer's crotch area 115, which can extend downward from about the transverse axis 112 near the pubic bone to just below the gluteus maximus. An absorbent garment can be configured to be worn over the wearer's crotch area 115.

Figure 5:
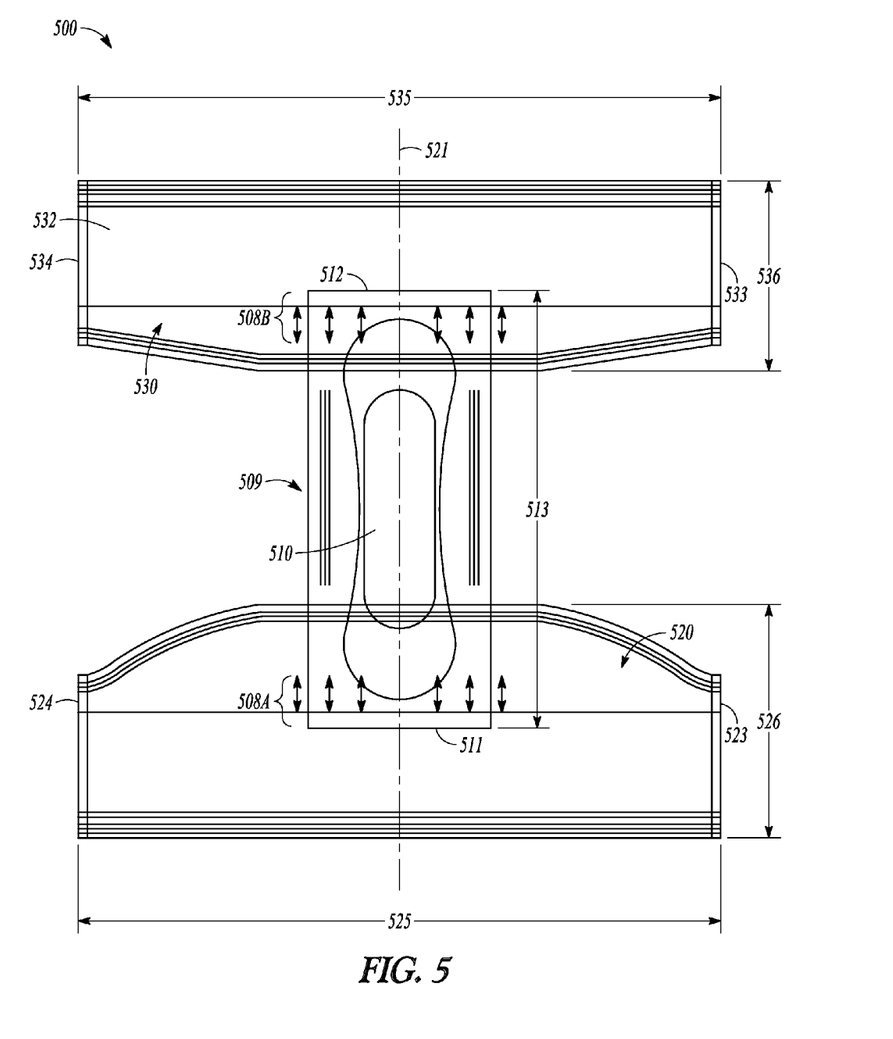
FIG. 5 illustrates generally an example of I-brief-style absorbent garment with a contraction region configured to extend or retract an absorbent core of the garment.

In some examples, an absorbent garment includes a pant-style garment that resembles a traditional cloth undergarment in size or shape. The pant-style garment can include a continuous waistband, such as can include elastic portions about the circumference of the waistband that secure the garment about the wearer's waist. In some examples, the absorbent garment is an I-brief-style garment, so-named because the garment resembles an "I" or hourglass shape when the article is extended or flattened. The I-brief-style garment can include a waistband area comprising different front and rear panels that are coupleable about the wearer's waist using a fastener (e.g., adhesive tab fasteners, hook-and-loop fasteners, or other similar coupling means). An example of I-brief-style garment is illustrated in the example of FIG. 5, described further below.

Either of the pant-style and I-brief-style garments can include an absorbent panel assembly that is configured to be disposed in the wearer's crotch area 115 when the garment is worn. The absorbent panel assembly can include at least one absorbent core, such as can include a polymer, fluff, or pulp material that is configured to absorb liquid. Generally, the absorbent core(s) can be positioned in the absorbent panel assembly in an area that will receive liquids and expand in such a manner as to be least disruptive to the wearer. For example, the absorbent core(s) can be substantially disposed in front of or in back of the wearer, such as with a minimal amount of absorbent core material disposed between the wearer's legs.

When worn, the absorbent core is generally held in place by virtue of its fixed position relative to the absorbent panel assembly, and by virtue of a fixed connection between the absorbent panel assembly and a waistband assembly. Accordingly, placement of the absorbent core, and of the absorbent panel assembly, substantially depends on how the waistband assembly interacts with the wearer's waist and crotch area 115. In some examples, even when a garment is properly sized (e.g., about the wearer's waist), the absorbent panel assembly and/or absorbent core portion can sag or can otherwise be decoupled from, or separated from, the wearer's body. The disconnection between the wearer's body and the absorbent garment can cause discomfort for the wearer, and can cause the wearer to think or feel that the garment is out of place, improperly sized, or dysfunctional. As a result, the wearer may select a different garment, or a differently sized garment (e.g., even an improperly sized garment). Because the absorbent panel assembly or a portion thereof is not in direct contact with the body, the wearer may have a nagging desire or instinct to adjust or pull the garment upward, into the wearer's crotch region 115. In some examples, the wearer wishes to ensure that there is at least a noticeable physical connection between the body and the garment. Such proximity between the wearer body and the garment can provide the wearer with a sense of confidence that the garment will absorb bodily excretions, or that fluids will not leak.

In an example, an absorbent garment can include a contraction region that is configured to extend and retract in such a manner as to draw an absorbent panel assembly, including an absorbent core portion, upward into the wearer's crotch region 115, such as between the wearer's legs. The contraction region can comprise an extensible and retractable portion of one or more of the absorbent panel assembly and the waistband assembly. In an example, the contraction region can be adjacent to, or can include, a portion of the absorbent core. The contraction region can be configured to draw or force the absorbent core toward an upper edge of the waistband assembly to provide that, even in a relaxed state, the absorbent core of the garment is closely positioned at, near, or even against an expected insult area when the garment is worn.

The examples 101 and 102 of FIGS. 1A and 1B further illustrate a longitudinal axis 121 of an absorbent core. In an example, an absorbent core can have a longitudinal axis 121 that can substantially coincide with extension and retraction directions of the garment. These directions can be substantially parallel to the height axis 110 of the wearer when the garment is worn.

Figure 2:
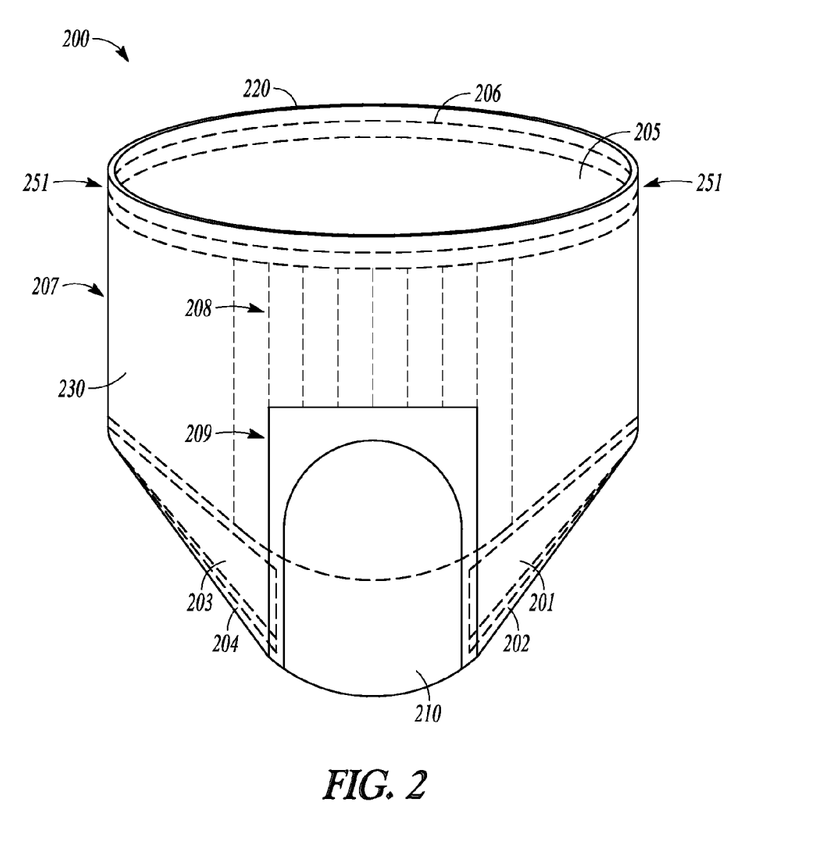
FIG. 2 illustrates generally an example of an absorbent garment with a first contraction region configured to extend or retract an absorbent core of the garment.

Referring now to FIG. 2, an example of an absorbent garment 200 with a contraction region 208 is shown. The absorbent garment 200 can include a brief-style garment or an I-brief-style garment (e.g., in an assembled state, as shown). The absorbent garment 200 can be configured for single-use and can be sized to fit children or adults. In some examples, similar absorbent garment configurations can be provided for use with animals, such as dogs, cats, primates, or other animals.

The absorbent garment 200 includes an absorbent panel assembly 209 that can include an absorbent core 210. The absorbent core 210 can be configured to receive or absorb human or animal bodily excretions. The absorbent panel assembly 209 can include, among other things, one or more of a liquid-permeable body-side layer, the absorbent core 210, or a substantially liquid-impervious backsheet. The absorbent core 210 can be configured to absorb various bodily fluids and excrement. In an example, the absorbent core 210 includes a super absorbent polymer (SAP) that is configured to soak up and retain fluid.

The absorbent garment 200 includes first and second leg openings 201 and 203, and a torso opening 205. The absorbent garment 200 is thus configured to be worn like a traditional undergarment, such as where a wearer can step each foot through one of the first and second leg openings 201 and 203, and the wearer can pull the garment up and secure the garment about his or her waist. The absorbent garment 200 can include extensible and retractable features 202 and 204 (e.g., elastic strands) around the leg openings 201 and 203, respectively, to ensure leg portions of the garment are coupled against or near the wearer's legs or body (e.g., to prevent leakage).

The absorbent garment 200 can include a waistband assembly 207, such as comprising a front portion 230 and a rear portion 220. In an example, the absorbent garment 200 can include an extensible and retractable feature 206, such as around the torso opening 205, that can be configured to couple the absorbent garment 200 to a wearer's torso. In an example, the front and rear portions 230 and 220 correspond to separate panels of the garment (e.g., in an I-brief-style garment) that can overlap or can be otherwise joined using a fastener, as described above. In some examples, the front and rear portions 230 and 220 are continuous (e.g., seamless, such as in a pant-style garment).

The absorbent garment 200 can include one or more extensible and retractable portions that, in a relaxed or unworn state, are contracted or retained in a relatively small or compact state. For example, at least one of the front portion 230 and the rear portion 220 can be extensible and retractable, such as in one, two, or more different directions. In a relaxed or unworn state, the at least one portion maintains a contracted or minimized configuration that can be stretched or extended when worn, such as to accommodate a wearer's body.

In an example, the front and rear portions 230 and 220 can comprise a nonwoven cloth material that can be stretchably extended in at least first and second directions, the first direction being substantially orthogonal to the second direction. In an example, when the absorbent garment 200 is worn about a wearer's torso, the extensible and retractable portions can provide an elastic support force around the wearer's waist to secure or conform the waistband assembly 207 of the absorbent garment 200 to the wearer's waist. This elastic support force can be provided in a substantially inward or circumferential direction 251, such as toward a wearer's body, or about the transverse axis 112 of the body. That is, the elastic support force can be provided about the wearer's waist in much the same manner as the constricting force provided by an elastic band about an upper edge of a traditional non-disposable or cloth undergarment.

In addition to, or alternatively to, providing the elastic support force about the wearer's waist, an extensible and retractable portion can provide an additional elastic force that can draw the absorbent panel assembly 209 of the absorbent garment 200 upward, toward or against a wearer's body, and into the wearer's crotch region 115. That is, the extensible and retractable portion can provide an elastic force substantially along the wearer's height axis 110 when the garment is worn.

The absorbent garment 200 can be simultaneously secured to a wearer's torso and drawn upward, relative to the wearer, toward the wearer's crotch region, to securely couple the garment to the wearer, such as using the extensible and retractable portions comprising the rear and front portions 220 and 230. By more securely coupling the absorbent garment 200 to the wearer, the effectiveness of the absorbent core 210 of the garment can be improved, for example, because the absorbent core can be more precisely located in insult areas, proximal to body portions of interest. In some examples, a wearer of the absorbent garment 200 can be more confident in wearing the garment because the effectiveness of absorption is improved and the likelihood of experiencing an accident or leak from the garment is reduced.

In an example, the absorbent garment 200 includes extensible and retractable features in the contraction region 208. The extensible and retractable features can include, among other things, elastic strands, elastic ribbons, or woven or non-woven cloth or polymer materials that are stretchable. When the absorbent garment 200 is worn, the extensible and retractable features in the contraction region 208 can be oriented in the direction of the wearer's height axis 110. In an example, the direction of the wearer's height axis 110 is substantially orthogonal to the above-described elastic support force that can be provided in a substantially inward or circumferential direction 251, such as toward a wearer's body, or about the transverse axis 112 of the body. The extensible and retractable features in the contraction region 208 can be arranged substantially parallel to a longitudinal or elongate dimension of the absorbent core 210.

In an example, at least one of the front and rear portions 230 and 220 of the absorbent garment 200 is extensible and retractable substantially in the direction of the wearer's height axis 110, and the same or a different at least one of the front and rear portions 230 and 220 is extensible and retractable substantially in the direction of the wearer's transverse axis 112. The different directions of extensibility and retractibility can correspond to different elastic moduli. For example, a first elastic force can act upon the absorbent core 210 to draw the core upward toward and into a wearer's crotch region. A lesser or greater second elastic force can act about the wearer's torso (e.g., in the direction of or about the transverse axis 112) to secure the absorbent garment 200 about the wearer's waist.

In an example, the front and rear portions 230 and 220 of the absorbent garment 200 are sufficiently sized such that at least a portion of the waistband assembly 207 is secured above a wearer's hips. In an example, a wearer can have an hourglass-type body shape, wherein the wearer's body is at a widest point about the hips. When the waistband assembly 207 reaches above the hips, at least an upper edge portion of the waistband assembly 207 can contract about a portion of the wearer's torso that has a smaller circumference than the portion of the wearer's torso that includes the wearer's hips. As such, the upper edge portion of the waistband assembly 207 that is contracted about the smaller circumference above the hips can act as an anchor or pivot that can secure the absorbent garment 200 vertically relative to the wearer's body. The extensible and retractable features in the contraction region 208 can be coupled to this upper edge portion of the waistband assembly 207 such that the extensible and retractable features have an anchor or base point toward which to draw all or a portion of the absorbent panel assembly 209.

Figure 3:
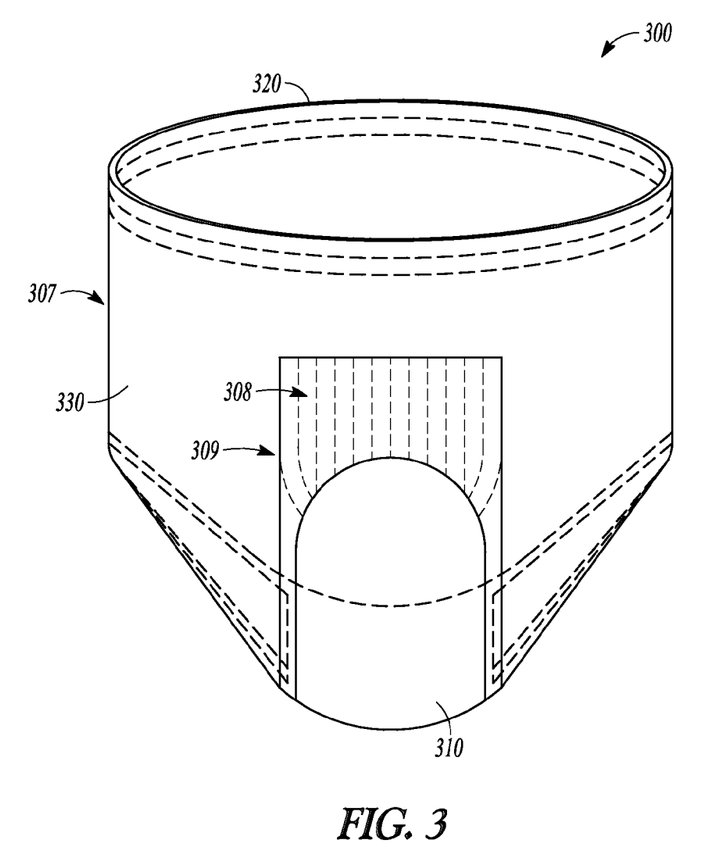
FIG. 3 illustrates generally an example of an absorbent garment with a second contraction region configured to extend or retract an absorbent core of the garment.

As shown in the example absorbent garment 200 of FIG. 2 and as described above, the contraction region 208 can be located on or in the front and rear portions 230 and 220 of the waistband assembly 207. FIG. 3 illustrates generally an example of an absorbent garment 300 that includes a contraction region 308 that is located on or contained in the absorbent panel assembly 309. That is, the contraction region 308 can be fully or at least partially contained within the absorbent panel assembly 309. In the illustrated example of the absorbent garment 300, the absorbent panel assembly 309 overlaps with at least the front portion 330 of the waistband assembly 307; however, other, non-overlapping configurations are also possible. In another example, a contraction region can comprise portions of the absorbent panel assembly 309 and one or both of the front and rear portions 330 and 320 of the waistband assembly 307.

Depending on the configuration of the absorbent garment and a wearer's particular incontinence issue, the upward-acting force may be more desired or more essential toward the front or rear of the garment. For example, a wearer with urinary incontinence can desire a close or contacting fit at or near the front portion 330 of the absorbent garment, but can further desire a more loose fit near the rear portion 320 of the absorbent garment. In this scenario, the contraction region may cover only those portions of the absorbent panel assembly 309 corresponding to the front of the garment, and/or may also cover the front portion 330 of the waistband assembly 307.

Figure 4:
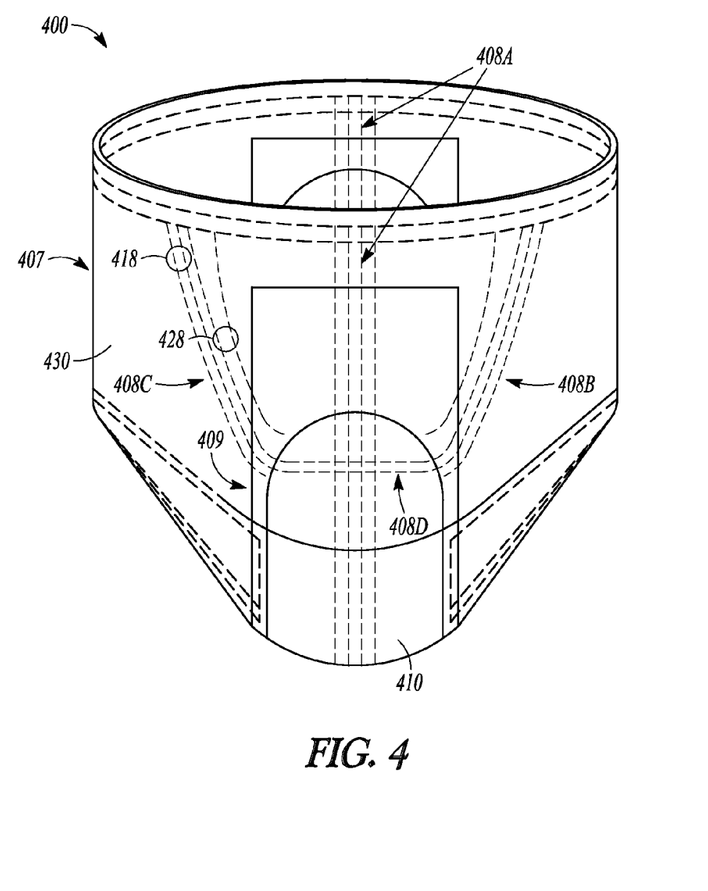
FIG. 4 illustrates generally an example of an absorbent garment with multiple contraction regions configured to extend or retract an absorbent core of the garment.

FIG. 4 illustrates generally an example of an absorbent garment 400 that includes multiple contraction regions 408A, 408B, 408C, and 408D. A first contraction region 408A can extend along a longitudinal axis of an absorbent panel assembly 409. In an example, the first contraction region 408A extends continuously and substantially between opposite upper edges of a waistband assembly 407 and across the absorbent panel assembly 409, such as along its longitudinal axis. In an example, the first contraction region 408A comprises an extensible and retractable material, or includes one or more elastic elements that are extensible and retractable along the direction of the longitudinal axis of the absorbent panel assembly. When worn, the contraction region 408A acts to draw the absorbent panel assembly 409, and an absorbent core 410, upward, toward the upper edges of the waistband assembly 407, and into the wearer's crotch region 115.

In an example, the first contraction region 408A includes elastic elements that extend from the waistband assembly and over one or more portions of the absorbent panel assembly 409, such as without continuously covering the absorbent panel assembly 409. For example, there can be a "dead zone" without any elastic elements or extensible and retractable material (e.g., acting in the longitudinal direction) in a central portion of the absorbent panel assembly 409. In this example, the first contraction region 408A can elastically act on the end portions of the absorbent panel assembly 409 to provide an upward force.

The second and third contraction regions 408B and 408C can extend between the absorbent core 410 of the absorbent panel assembly 409 and the upper edge of the waistband assembly 407. In an example, the second and third contraction regions 408B and 408C can include an arrangement of elastic elements that is flared, or that extends from a central portion of the garment (e.g., a central portion of the absorbent core 410) toward an outer or hip-region of the waistband assembly 407. In the example of FIG. 4, elastic elements in the second and third contraction regions 408B and 408C can be coupled to one or more of the absorbent core 410 or another portion of the absorbent panel assembly 409, and can extend outwardly, away from the longitudinal axis of the absorbent core 410, as the elastic elements approach the waistband upper edge.

In an example, the absorbent garment 400 includes a fourth contraction region 408D that extends transversely across the absorbent core 410 and substantially between ends of the second and third contraction regions 408B and 408C. In an example, one or more continuous elastic elements can be used to provide extension and retraction of the absorbent panel assembly 409 by spanning the second, third, and fourth contraction regions 408B, 408C, and 408D.

In an example, a contraction region can include elastic elements that have different characteristics, or are arranged to provide different elastic densities in different portions of the garment. For example, the absorbent garment 400 can include, in each of the second and third contraction regions 408B and 408C, a first cluster of elastic elements 418 having a first density or elasticity, and a second cluster of elastic elements 428 having a second density or elasticity. The first density can be greater than the second density. This configuration can provide a relatively greater magnitude of elastic force that draws the absorbent panel assembly 409 toward a wearer's crotch area by pulling the absorbent panel assembly 409 upward and toward the wearer's hips. In contrast, the lesser second density can provide a lesser magnitude of elastic force, but can nonetheless act to draw the absorbent panel assembly 409 toward the wearer's crotch area by pulling the absorbent panel assembly 409 more vertically upward (e.g., in the direction of the axis 121).

Any of the contraction regions of the absorbent garments described herein can include sub-regions that provide different degrees (i.e., magnitudes) of extension or retraction forces. For example, the first contraction region 408A can include an extensible and retractable first sub-region that provides a first force, such as corresponding to areas at or near a central or longitudinal axis of the absorbent core 410. The first contraction region 408A can include an extensible and retractable second sub-region that provides a second force, such as corresponding to areas that are adjacent to or spaced apart from the axis of the absorbent core 410.

FIG. 5 illustrates generally an example of an I-brief-style absorbent garment 500 in a substantially extended or flattened configuration. The example of FIG. 5 includes an absorbent panel assembly 509, a rear panel assembly 520, and a front panel assembly 530. When worn, corresponding side edges 524 and 534 of the rear and front panel assemblies 520 and 530, respectively, can be joined or overlapped (e.g., using a fastener; not shown) to form a first leg opening (see, e.g., FIG. 2 at 201). Corresponding side edges 523 and 533 can similarly be joined or overlapped to form a second leg opening (see, e.g., FIG. 2 at 203). In an example, the rear and front panel assemblies 520 and 530 can be similar or dissimilar. For example, the panel assemblies can have similar or dissimilar sizes, shapes, or constituent materials. For example, as shown in FIG. 5, the front panel assembly 530 can have a smaller area than the rear panel assembly 520.

The absorbent panel assembly 509 can extend between first and second ends 511 and 521 along an absorbent panel length 513. In an example, the absorbent panel assembly 509 includes an absorbent core 510 and can be coupled at or near the first and second ends 511 and 521 to the rear and front panel assemblies 520 and 530, respectively. The absorbent core 510 can be an elongate structure, such as comprising absorbent pulp or polymer materials. The absorbent core 510 can have a longitudinal axis 521 that extends along the absorbent panel length 513. In some examples, the longitudinal axis 521 bisects the rear and front panel assemblies 520 and 530 when the absorbent panel assembly 509 is affixed to the rear and front panels. In an example, a portion of the rear panel assembly 520 can be overlapped by an end portion (e.g., comprising the first end 511) of the absorbent panel assembly, and a portion of the front panel assembly 530 can be overlapped by an opposite end portion (e.g., comprising the second end 512) of the absorbent panel assembly.

The back and front panel assemblies 520 and 530 can comprise multiple different materials. In an example, a panel assembly can include an inner, or body-side, material, such as a non-woven cloth material. A panel assembly can include an outer material, such as a non-woven cloth material, or a plastic or plasticized material that is impervious to liquids. In an example, at least one of the back and front panel assemblies 520 and 530 or the absorbent panel assembly 509 includes one or more extensible and/or retractable materials, such as can be incorporated into or bonded with at least one of the inner and outer materials.

In an example, at least one of the back and front panel assemblies 520 and 530 can include a stretch film or other elastic material. The stretch film or other elastic material can be disposed along and affixed to a panel assembly in a direction that corresponds to a length of the panel (e.g., substantially orthogonal to the longitudinal axis 521 when the panel is affixed to the absorbent panel assembly 509). The stretch film or other elastic material can comprise all or a portion of a panel assembly. For example, as illustrated in the example of FIG. 5, the front panel assembly 530 can include an elastomeric film 532. The elastomeric film 532 can, in an example, be ultrasonically-bonded to a base material of the panel assembly (e.g., to an inner or outer layer of the panel assembly), and the elastomeric film 532 can span all or a portion of a width 535 of the front panel assembly 530. In an example, the elastomeric film 532 is stretchable in at least one direction, such as a direction that is one of substantially parallel to or orthogonal to the longitudinal axis 521 (e.g., when the absorbent panel assembly 509 is affixed to the rear panel assembly 520).

In an example, the elastomeric film 532 can include one or more unidirectionally stretchable layers that can provide extension and retraction in at least first and second directions (e.g., substantially orthogonal directions). In an example, the elastomeric film 532 can be a single, bidirectionally stretchable layer that can provide extension and retraction in the first and second directions. In an example, the elastomeric film 532 can be extended or stretched before it is affixed to the front panel assembly 530 such that when the film is released, the front panel assembly 530 contracts. Although the above discussion of the elastomeric film 532 is provided in the context of the front panel assembly 530, a similar elastomeric film can be applied to the rear panel assembly 520. In an example, any one or more of a panel assembly inner material, outer material, or elastic material can be stretched in any one or more directions during assembly of the absorbent garment 500.

In an example, a non-woven cloth material that comprises a portion of one or more of the rear and front panel assemblies 520 and 530, or that comprises a portion of the absorbent panel assembly 509, can be configured to provide extension and retraction in one or more directions. That is, the non-woven cloth material can itself be stretchable or elastic in one or more directions of interest. Thus, one or more of the inner or outer materials comprising the stretchable non-woven material can itself provide extension and/or retraction sufficient to draw the absorbent core 510 substantially upward and toward a wearer's crotch region when the garment is worn.

In an example, the rear or front panel assemblies 520 or 530 can include respective rear or front contraction regions 508A or 508B. In the example of the front panel assembly 530, the panel includes the front contraction region 508B, such as can include at least a portion (designated in the example of FIG. 5 by a series of parallel arrows) of the panel that is substantially extensible and retractable in the direction of the longitudinal axis 521 of the absorbent core 510. The contraction region 508B can be substantially adjacent to, or overlapping with, one or both of the absorbent core 510 and the absorbent panel assembly 509 such that the contraction region 508B acts to retract the absorbent core 510 toward an upper edge of the front panel assembly 530 when the garment is worn. Similarly, the contraction region 508A can be substantially adjacent to, or overlapping with, one or both of the absorbent core 510 and the absorbent panel assembly 509 such that the contraction region 508A acts to retract the absorbent core 510 toward an upper edge of the rear panel assembly 520 when the garment is worn. In the example of FIG. 5, the series of arrows illustrated in the contraction regions 508A and 508B illustrate generally the direction of the extensible and retractable forces that can act on the absorbent core 510 and the absorbent panel assembly 509.

In an example, one or both of the rear and front panel assemblies 520 and 530 of the absorbent garment 500 includes a contraction region. In an example that includes contraction regions in both panel assemblies, the absorbent core 510 can be pulled toward each of the rear panel assembly 520 and the front panel assembly 530 by the elastic or stretchable elements comprising the respective panel assemblies.

Figure 6:
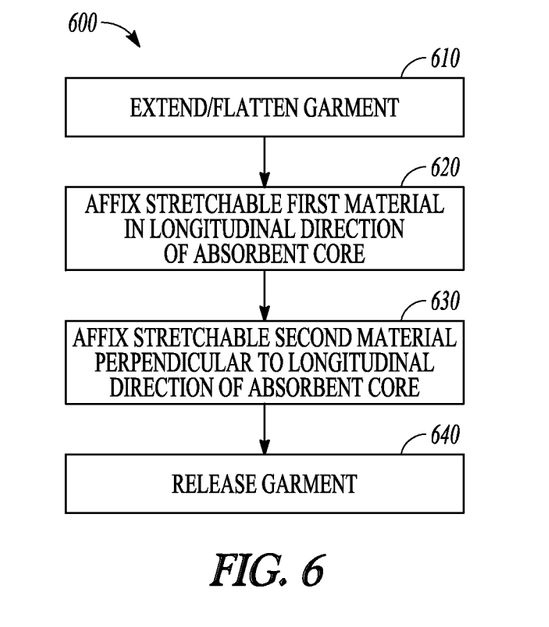
FIG. 6 illustrates generally an example that can include affixing a stretchable material to an absorbent garment.
Figure 7:
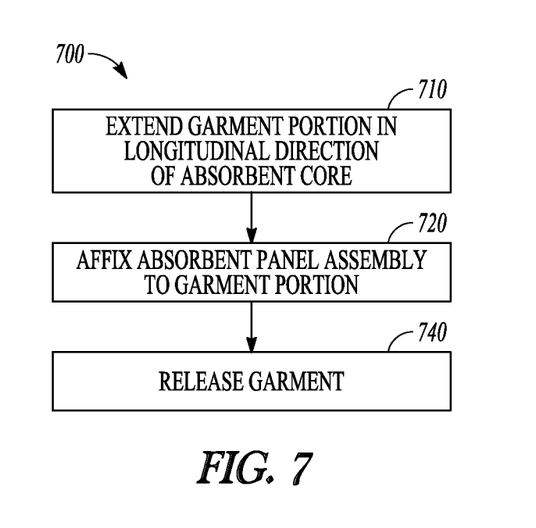
FIG. 7 illustrates generally an example that can include affixing an absorbent panel assembly to an extended absorbent garment.

Referring now to FIGS. 6 and 7, several methods for preparing an absorbent garment with an extensible and retractable core are described. FIG. 6 illustrates generally an example of a method 600 that can include preparing an absorbent garment with an extensible and retractable core. At 610, a garment, or a portion of a garment, can be flattened or extended. For example, where a garment panel assembly includes a stretchable non-woven cloth material, the cloth material can be flattened or extended across a work surface. The garment panel assembly can be stretched to some predetermined or specified maximum dimension (e.g., to 120% of the assembly's non-extended width) along a particular direction, or the portion of the absorbent garment can be stretched until some predetermined or specified maximum elastic force is attained.

At 620, a stretchable first material can be affixed to the garment (e.g., to the garment panel assembly) in a direction that is substantially parallel to a longitudinal direction of the absorbent core. The stretchable first material that is affixed at 620 can be affixed near or adjacent to the absorbent core portion that is to be made extensible and retractable. The stretchable first material can be configured to act upon the absorbent core to draw the absorbent core toward a waistband portion of the garment when the garment is worn.

At 630, a stretchable second material can be affixed to the garment (e.g., to the garment panel assembly) in a direction that is substantially orthogonal to the longitudinal direction of the absorbent core. The stretchable second material that is affixed at 630 can be the same or different material type as the first material that is affixed at 620. The stretchable second material affixed at 630 can be extensible and retractable about a wearer's waist or torso when the garment is worn. The stretchable first and second materials themselves can be affixed at 620 and 630, respectively, in one of a relaxed or extended state. Once the first and second materials are affixed to the garment to provide extension and retraction in at least two directions, the garment can be released at 640, such as for use or for further processing (e.g., printing, packaging, etc.).

FIG. 7 illustrates generally an example of a method 700 that can include affixing an absorbent panel assembly to a stretched or extended absorbent garment. At 710, an absorbent garment or a portion thereof can be extended substantially in a direction of a longitudinal axis of an absorbent core of the absorbent garment. For example, the extended portion can include a rear or front panel of the absorbent garment. The extended portion of the absorbent garment can be stretched to some predetermined or specified maximum dimension (e.g., to 120% of the garment's or garment portion's non-extended width) along a particular direction, or the extended portion of the absorbent garment can be stretched until some predetermined or specified maximum elastic force is attained.

At 720, with the garment portion extended, an absorbent panel assembly can be affixed to the extended garment. As a result, when the garment portion is released, the garment portion can retract or recoil, thereby withdrawing the absorbent panel assembly toward the relaxed garment portion. At 740, the extended garment can be released, such as for use or for further processing (e.g., printing, packaging, etc.).

The absorbent garments described herein can be configured to securely couple an absorbent portion of an absorbent garment to a wearer's body. In an example, the absorbent garments described herein can be configured to more accurately locate an absorbent portion of an absorbent garment in a target area of the wearer's crotch region than can be provided using a traditional absorbent garment without a contraction region. In some examples, absorbent garments with an extensible and retractable absorbent panel assembly can be comprised of a lesser quantity of the panel materials than is used in a comparable "traditional" absorbent garment because of the more targeted positioning and improved fit. As a result, in some examples, the absorbent garments described herein can be manufactured for a lesser cost than traditional absorbent garments.

Notes & Examples

Example 1 can include or use subject matter such as an apparatus, or a method of making an apparatus, such as can include or use a disposable absorbent garment. In Example 1, the disposable absorbent garment can comprise or use, among other things, a waistband assembly configured to be worn about a waist of a subject and an absorbent panel assembly. The absorbent panel assembly can have first and second ends that can be coupled to the waistband assembly. The absorbent panel assembly can include a liquid-pervious body-side layer, a liquid impervious external layer, and an absorbent core positioned between the body-side and external layers. In Example 1, at least one of the absorbent panel assembly or the waistband assembly can include a first contraction region that is configured to be extensible and retractable along a longitudinal axis of the absorbent core.

Example 2 can include, or can optionally be combined with the subject matter of Example 1, to optionally include the first contraction region configured to elastically retract the absorbent core toward the waistband assembly.

Example 3 can include, or can optionally be combined with the subject matter of Example 2, to optionally include the waistband assembly, wherein the waistband assembly comprises all or a portion of the first contraction region.

Example 4 can include, or can optionally be combined with the subject matter of Example 3, to optionally include the waistband, wherein the waistband assembly comprises a second contraction region that is configured to be extensible and retractable along a direction that is substantially orthogonal to the longitudinal axis of the absorbent core.

Example 5 can include, or can optionally be combined with the subject matter of Example 4, to optionally include the first and second contraction regions having different elastic moduli.

Example 6 can include, or can optionally be combined with the subject matter of one or any combination of Examples 1 through 5 to optionally include the absorbent panel assembly, wherein the absorbent panel assembly comprises all or a portion of the first contraction region.

Example 7 can include, or can optionally be combined with the subject matter of one or any combination of Examples 1 through 6 to optionally include the absorbent panel assembly and the waistband assembly, wherein each of the absorbent panel assembly and the waistband assembly comprises at least a portion of the first contraction region.

Example 8 can include, or can optionally be combined with the subject matter of one or any combination of Examples 1 through 7 to optionally include the first contraction region, the first contraction region including elastic elements arranged substantially parallel to the longitudinal axis of the absorbent core.

Example 9 can include, or can optionally be combined with the subject matter of Example 8 to optionally include the elastic elements, wherein at least a portion of the elastic elements in the first contraction region have a different elastic modulus than the other elastic elements in the first contraction region.

Example 10 can include, or can optionally be combined with the subject matter of one or any combination of Examples 8 or 9 to optionally include the elastic elements, wherein the elastic elements are arranged across portions of one or both of the waistband assembly and the absorbent panel assembly.

Example 11 can include, or can optionally be combined with the subject matter of one or any combination of Examples 8 through 10 to optionally include the waistband assembly, wherein the waistband assembly comprises first and second hip regions corresponding to the hips of the subject when the garment is worn, and wherein the first contraction region can include elastic elements arranged to extend substantially between the absorbent core and respective ones of the first and second hip regions of the waistband assembly.

Example 12 can include, or can optionally be combined with the subject matter of one or any combination of Examples 8 through 11 to optionally include the elastic elements, wherein at least a portion of the elastic elements extend over the absorbent core.

Example 13 can include, or can optionally be combined with the subject matter of one or any combination of Examples 1 through 12 to optionally include the first contraction region, wherein the first contraction region comprises a non-woven cloth material. In Example 13, the non-woven cloth material can be configured to substantially unidirectionally extend and retract.

Example 14 can include, or can optionally be combined with the subject matter of one or any combination of Examples 1 through 13 to optionally include the first and second ends of the absorbent panel assembly are coupled to the waistband assembly at substantially opposite sides of the waistband assembly when the garment is worn. For example, the first end is coupled to a side of the waistband assembly corresponding to a wearer's front side, and the second end is coupled to a side of the waistband assembly corresponding to the wearer's rear side.

Example 15 can include, or can optionally be combined with the subject matter of one or any combination of Examples 1 through 14 to optionally include the waistband assembly, including a front panel and a separate rear panel. In Example 15, the first end of the absorbent panel assembly can be coupled to the front panel, and the second end of the absorbent panel assembly can be coupled to the rear panel.

Example 16 can include, or can optionally be combined with the subject matter of Example 15 to optionally include one of the front panel and the rear panel, wherein the one panel includes a fastener configured to adhere to the other of the front panel and the rear panel.

Example 17 can include, or can optionally be combined with the subject matter of Example 16 to optionally include the fastener, wherein the fastener can be, among other types, one of an adhesive tape type fastener or a hook-and-loop type fastener.

Example 18 can include, or can optionally be combined with the subject matter of one or any combination of Examples 1 through 17 to optionally include the first contraction region, wherein the first contraction region is disposed adjacent to the absorbent core. In Example 18, the first contraction region can optionally be coupled to or overlapping with the absorbent core.

Example 19 can include, or can optionally be combined with the subject matter of one or any combination of Examples 1 through 18 to optionally include a front panel having a longitudinal first length and a first width, and a rear panel having a longitudinal second length and a second width. Example 19 can optionally include an absorbent panel assembly having a longitudinal third length that can extend from an absorbent panel assembly first end to an absorbent panel assembly second end. In Example 19, the absorbent panel assembly can include an absorbent region that extends along a portion of the third length. In Example 19, at least one of the first and second lengths can be oriented substantially transverse to the third length. In Example 19, the first end of the absorbent panel assembly can be coupled to the front panel, or the second end of the absorbent panel assembly can be coupled to the rear panel. In Example 19, at least one of the front and rear panels can include a contraction region, positioned adjacent to, overlapping with, or otherwise near to a respective one of the first and second ends of the absorbent panel assembly. In Example 19, the contraction region can be extensible and retractable in the direction of the third length and can be configured to retract the absorbent panel assembly toward the at least one of the front and rear panels (e.g., corresponding to a front or rear side of a wearer when the garment is worn).

Example 20 can include, or can optionally be combined with the subject matter of Example 19 to optionally include the front and rear panels, wherein the front and rear panels include respective front and rear contraction regions positioned adjacent to, overlapping with, or near the first and second ends, respectively, of the absorbent panel assembly.

Example 21 can include, or can optionally be combined with the subject matter of one or any combination of Examples 19 or 20 to optionally include at least one of the front or rear panels is extensible and retractable in the direction of the first or second lengths, respectively.

Example 22 can include, or can optionally be combined with the subject matter of one or any combination of Examples 19 through 21 to optionally include the front and rear panels configured to be extensible and retractable in the direction of the first and second lengths, respectively.

Example 23 can include, or can optionally be combined with the subject matter of one or any combination of Examples 19 through 22 to optionally include the ends of the front panel assembly at the extents of the first length are fixedly coupled to the ends of the rear panel assembly at the extents of the second length.

Example 24 can include, or can optionally be combined with the subject matter of one or any combination of Examples 19 through 23 to optionally include at least one of the front and rear panels includes a fastener configured to adhere to the other of the front and rear panels.

Example 25 can include, or can optionally be combined with the subject matter of one or any combination of Examples 1 through 24 to include, subject matter (such as an apparatus, a method, a means for performing acts, or a machine readable medium including instructions that, when performed by the machine, that can cause the machine to perform acts), such as can include a method for manufacturing a disposable absorbent garment with an absorbent core that is retractable toward a subject body when the absorbent garment is worn. Example 25 can include extending at least a portion of an absorbent garment into a substantially planar orientation to provide an affixation surface. Example 25 can optionally include affixing a substantially unidirectionally-stretchable first material to the portion of the absorbent garment comprising the affixation surface, including affixing the first material in a first direction that is substantially parallel to a longitudinal axis of an absorbent core of the absorbent garment. Example 25 can optionally include affixing a substantially unidirectionally-stretchable second material to the same or a different portion of the absorbent garment comprising the affixation surface, including affixing the second material in a second direction that is substantially orthogonal to the first direction.

Example 26 can include, or can optionally be combined with the subject matter of Example 25 to optionally include extending at least a portion of the absorbent garment into the substantially planar orientation, including extending the absorbent garment in the first and second directions.

Example 27 can include, or can optionally be combined with the subject matter of one or any combination of Examples 25 or 26 to optionally include extending at least a portion of the absorbent garment into the substantially planar orientation, including extending the absorbent garment in the first direction, substantially parallel to the longitudinal axis of the absorbent core of the absorbent garment.

Example 28 can include, or can optionally be combined with the subject matter of one or any combination of Examples 25 through 27 to optionally include extending at least a portion of the absorbent garment, including stretching a nonwoven cloth material comprising the portion of the absorbent garment.

Example 29 can include, or can optionally be combined with the subject matter of one or any combination of Examples 25 through 28 to optionally include affixing the first and second materials to the absorbent garment, including extending an elastic strand from a relaxed state to an extended state, applying an adhesive to the elastic strand when the elastic strand is in the extended state, or affixing the elastic strand to the portion of the absorbent garment comprising the affixation surface.

Example 30 can include, or can optionally be combined with any portion or combination of any portions of any one or more of Examples 25 through 29 to include, subject matter that can include means for performing any one or more of the functions of Examples 25 through 29, or a machine-readable medium including instructions that, when performed by a machine, cause the machine to perform any one or more of the functions of Examples 25 through 29.

Each of these non-limiting examples can stand on its own, or can be combined in various permutations or combinations with one or more of the other examples in this document.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in any claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods or operate machinery to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A disposable absorbent garment, comprising:
   a waistband assembly configured to be worn about a waist of a subject; and
   an absorbent panel assembly having first and second ends that are coupled to the waistband assembly, the absorbent panel assembly including a liquid-pervious body-side layer, a liquid impervious external layer, and an absorbent core positioned between the body-side and external layers;
   wherein the absorbent panel assembly and the waistband assembly include a first contraction region that extends continuously between opposite upper edge regions of the waistband assembly and across the absorbent panel assembly;
   wherein the first contraction region is configured to be extensible and retractable along a longitudinal axis of the absorbent core; and
   wherein an extensibility characteristic of the first contraction region along a central portion of the longitudinal axis of the absorbent core is different than an extensibility characteristic of the first contraction region outside of the central portion of the longitudinal axis of the absorbent core.

2. The disposable absorbent garment of claim 1, wherein the first contraction region is configured to elastically retract the absorbent core toward the waistband assembly.

3. The disposable absorbent garment of claim 1, wherein the waistband assembly further comprises a second contraction region that is configured to be extensible and retractable along a direction that is substantially orthogonal to the longitudinal axis of the absorbent core.

4. The disposable absorbent garment of claim 3, wherein the first and second contraction regions have different elastic moduli.

5. The disposable absorbent garment of claim 1, wherein the first contraction region comprises multiple discrete elastic elements arranged substantially parallel to the longitudinal axis of the absorbent core.

6. The disposable absorbent garment of claim 5, wherein at least a portion of the multiple discrete elastic elements in the first contraction region are aligned with the central portion of the longitudinal axis of the absorbent core and have a different elastic modulus than the other elastic elements in the first contraction region outside of the central portion of the longitudinal axis of the absorbent core.

7. The disposable absorbent garment of claim 1, wherein the waistband assembly comprises first and second hip regions corresponding to the hips of the subject when the garment is worn, and wherein the absorbent panel assembly and the waistband assembly include a second contraction region that extends away from the longitudinal axis of the absorbent core and toward upper edge regions of the waistband assembly at the first and second hip regions.

8. The disposable absorbent garment of claim 7, wherein the second contraction region comprises multiple discrete elastic elements.

9. The disposable absorbent garment of claim 8, wherein the second contraction region comprises at least one elastic element that extends continuously from the upper edge of the first hip region of the waistband assembly, across the absorbent core transverse to the longitudinal axis of the absorbent core, and to the upper edge of the second hip region of the waistband assembly.

10. The disposable absorbent garment of claim 1, wherein the first contraction region comprises a non-woven cloth material, wherein the non-woven cloth material is configured to substantially unidirectionally extend and retract.

11. The disposable absorbent garment of claim 1, wherein the first and second ends of the absorbent panel assembly are coupled to the waistband assembly at substantially opposite sides of the waistband assembly when the garment is worn.

12. The disposable absorbent garment of claim 1, wherein the waistband assembly comprises a front panel and a separate rear panel, and wherein the first end of the absorbent panel assembly is coupled to the front panel, and the second end of the absorbent panel assembly is coupled to the rear panel.

13. A disposable absorbent garment, comprising:
   a front panel having a longitudinal first length and a first width;
   a rear panel having a longitudinal second length and a second width; and
   an absorbent panel assembly having a longitudinal third length extending from an absorbent panel assembly first end to an absorbent panel assembly second end, the absorbent panel assembly including an absorbent region that extends along a portion of the third length;

wherein the first and second lengths are oriented substantially transverse to the third length;

wherein the first end of the absorbent panel assembly is coupled to the front panel, and the second end of the absorbent panel assembly is coupled to the rear panel; and wherein at least one of the front and rear panels includes a contraction region that overlaps with one of the first and second ends of the absorbent panel assembly, wherein the contraction region is extensible and retractable in the direction of the third length and is configured to retract the absorbent panel assembly toward the at least one of the front and rear panels;

wherein an extensibility characteristic of the contraction region at a longitudinal axis of the absorbent panel assembly and in the direction of the longitudinal axis of the absorbent panel assembly is different than an extensibility characteristic of the contraction region in the direction of the longitudinal axis of the absorbent panel assembly and spaced apart from the longitudinal axis of the absorbent panel assembly.

14. The disposable absorbent garment of claim 13, wherein both of the front and rear panels include respective front and rear contraction regions that overlap with the first and second ends, respectively, of the absorbent panel assembly, and wherein the front and rear contraction regions are extensible in the direction of the longitudinal axis of the absorbent core.

15. The disposable absorbent garment of claim 14, wherein the front and rear contraction regions are extensible in a direction that is substantially parallel to the longitudinal third length.

16. The disposable absorbent garment of claim 13, wherein at least one of the front or rear panels is extensible and retractable in the direction of the first or second lengths, respectively.

17. The disposable absorbent garment of claim 13, wherein the front and rear panels are extensible and retractable in the direction of the first and second lengths, respectively.

18. The disposable absorbent garment of claim 13, wherein the ends of the front panel assembly at the extents of the first length are fixedly coupled to the ends of the rear panel assembly at the extents of the second length to form a pant-style garment.

19. The disposable absorbent garment of claim 13, wherein at least one of the front and rear panels includes a fastener configured to adhere to the other of the front and rear panels.

20. A method for manufacturing a disposable absorbent garment with an absorbent core that is retractable toward a subject body when the absorbent garment is worn, comprising:

extending an absorbent garment into a substantially planar orientation to provide an affixation surface along substantially the entire longitudinal length of the garment;

affixing a substantially unidirectionally-stretchable first material to the affixation surface, including affixing the first material in a first direction that substantially overlaps with a central longitudinal axis of an absorbent core of the absorbent garment;

affixing a substantially unidirectionally-stretchable second material to the affixation surface, including affixing the second material in the first direction and substantially adjacent to and spaced apart from the central longitudinal axis of an absorbent core of the absorbent garment; and affixing a substantially unidirectionally-stretchable third material to the same or a different portion of the absorbent garment comprising the affixation surface, including affixing the third material in a second direction that is substantially orthogonal to the first direction.

21. The method of claim 20, wherein the extending at least a portion of the absorbent garment into the substantially planar orientation includes extending the absorbent garment in the first and second directions.

22. The method of claim 20, wherein the extending at least a portion of the absorbent garment into the substantially planar orientation includes extending the absorbent garment in the first direction, substantially parallel to the longitudinal axis of the absorbent core of the absorbent garment.

23. The method of claim 20, wherein the extending at least a portion of the absorbent garment includes stretching a nonwoven cloth material comprising the portion of the absorbent garment.

24. The method of claim 20, wherein the affixing each of the first, second, and third materials to the absorbent garment includes:

extending an elastic strand from a relaxed state to an extended state;

applying an adhesive to the elastic strand when the elastic strand is in the extended state; and affixing the elastic strand to the portion of the absorbent garment comprising the affixation surface.

* * * * *